(12) United States Patent
Mauti et al.

(10) Patent No.: US 8,235,991 B2
(45) Date of Patent: Aug. 7, 2012

(54) ELECTROSURGICAL APPARATUS AND METHOD FOR COAGULATIVE TREATMENTS THROUGH RADIOFREQUENCY

(75) Inventors: Aldo Mauti, Aprilia LT (IT); Paolo Mauti, Aprilia LT (IT); Adriano De Majo, Rome (IT); Piero Rossi, Rome (IT)

(73) Assignees: LED S.p.A., Frosinone (IT); Consorzio I.P.O.TE.S.I., Rome (IT)

( * ) Notice: Subject to any disclaimer, the term of this patent is extended or adjusted under 35 U.S.C. 154(b) by 1381 days.

(21) Appl. No.: 11/791,311

(22) PCT Filed: Sep. 15, 2005

(86) PCT No.: PCT/IB2005/053039
§ 371 (c)(1),
(2), (4) Date: Aug. 15, 2007

(87) PCT Pub. No.: WO2006/059253
PCT Pub. Date: Jun. 8, 2006

(65) Prior Publication Data
US 2007/0299440 A1    Dec. 27, 2007

(30) Foreign Application Priority Data
Nov. 25, 2004  (IT) .............................. RM2004A0580

(51) Int. Cl.
*A61B 18/12* (2006.01)

(52) U.S. Cl. ........................................... 606/49; 606/34
(58) Field of Classification Search .............. 606/32–50
See application file for complete search history.

(56) References Cited

U.S. PATENT DOCUMENTS

| | | | | |
|---|---|---|---|---|
| 5,383,917 A | * | 1/1995 | Desai et al. | 607/102 |
| 5,536,267 A | * | 7/1996 | Edwards et al. | 606/41 |
| 5,620,481 A | * | 4/1997 | Desai et al. | 607/101 |
| 5,697,928 A | * | 12/1997 | Walcott et al. | 606/41 |
| 5,735,847 A | * | 4/1998 | Gough et al. | 606/41 |
| 5,888,198 A | | 3/1999 | Eggers et al. | |
| 6,049,737 A | * | 4/2000 | Simpson et al. | 607/119 |
| 6,237,605 B1 | * | 5/2001 | Vaska et al. | 128/898 |
| 6,730,078 B2 | * | 5/2004 | Simpson et al. | 606/34 |
| 7,294,143 B2 | * | 11/2007 | Francischelli | 607/105 |
| 7,553,309 B2 | * | 6/2009 | Buysse et al. | 606/41 |

FOREIGN PATENT DOCUMENTS

| | | |
|---|---|---|
| EP | 1 334 699 A | 8/2003 |
| WO | 03/005919 A | 1/2003 |
| WO | 2004/017851 A | 3/2004 |

* cited by examiner

*Primary Examiner* — Michael Peffley
*Assistant Examiner* — Ronald Hupczey, Jr.
(74) *Attorney, Agent, or Firm* — Nixon & Vanderhye P.C.

(57) ABSTRACT

An apparatus for electrosurgery (1) comprising a plurality of adjacent electrodes (2-5) arranged aligned and an electrosurgical current generator (6), connected or connectable to the electrodes (2-5) to induce the flowing of an electrosurgical current through the tissue portions interposed thereamong, wherein said generator (6) powers the electrodes (2-5) so that each electrode lies at a potential ($V_3$-$V_5$) greater than that of the electrode preceding it in the sequence.

43 Claims, 6 Drawing Sheets

FIG.6 atively ELECTROSURGICAL APPARATUS AND
METHOD FOR COAGULATIVE
TREATMENTS THROUGH
RADIOFREQUENCY

SEQUENCE LISTING (NOT APPLICABLE)

CROSS-REFERENCE TO RELATED
APPLICATION

This application is the U.S. national phase of International Application No. PCT/IB2005/053039 filed 15 Sep. 2005 which designated the U.S. and claims priority to Itialian Patent Application No. RM2004A000580 filed 25 Nov. 2004, the entire contents of each of which are hereby incorporated by reference.

STATEMENT REGARDING FEDERALLY
SPONSORED RESEARCH OR DEVELOPMENT (NOT APPLICABLE)

THE NAMES OF THE PARTIES TO A JOINT
RESEARCH AGREEMENT (NOT APPLICABLE)

INCORPORATION BY REFERENCE OF
MATERIAL SUBMITTED ON A COMPACT DISC (NOT APPLICABLE)

BACKGROUND OF THE INVENTION (1) Field of the Invention

The present invention relates to an electrosurgical apparatus mainly intended for the coagulative treatment, typically preliminary to resection, employing a plurality of electrodes connected to one or more generators and to a corresponding method.

(2) Description of Related Art Including Information Disclosed under 37 C.F.R. §1.97 and 1.98

Figure 1:
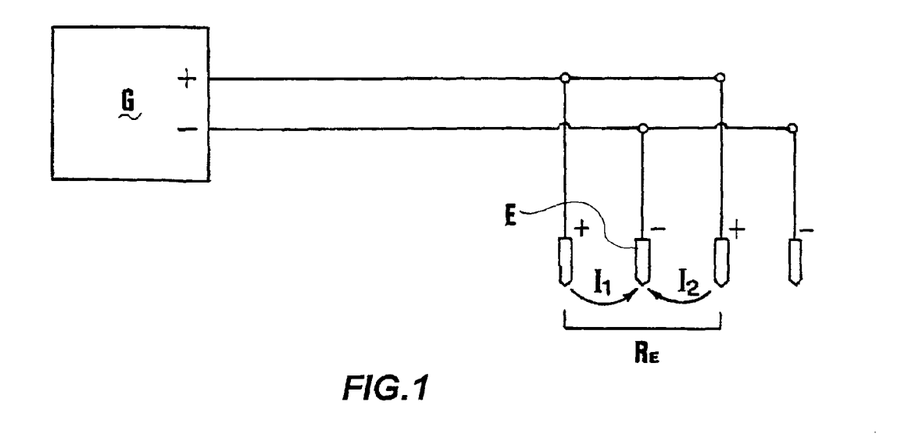
FIG. 1 shows a schematic depiction of a known system for electrosurgery.

In order to reduce or eliminate bleeding during and after a resective treatment of parenchymatous organs like liver, spleen, kidney, and so on, there are used apparatuses employing one or more generators, with a working frequency typically ranging from 200 kHz to 2 MHz, powering a plurality of electrodes, preferentially arranged in-line, in a bipolar mode. In particular, in said arrangement adjacent electrodes are connected to opposite poles of a generator, as schematically illustrated in FIG. 1, where the generator has been denoted by G. Therefore, between said adjacent electrodes there onset, through the tissue interposed thereamong, electrosurgical currents, denoted e.g. by $I_1$ and $I_2$ in FIG. 1, which flow into each intermediate electrode E. Optionally, the above-described configuration may employ a so-called "comb" electrode instead of a plurality of separate electrodes. Such a configuration is used, for example, to carry out linear or polygonal resections for the removal of damaged or diseased biological tissues, and in particular for the hepatic resection of tumours.

As mentioned above, due to the bipolar powering mode of the electrodes connected to the generator, at each intermediate electrode E there flow the currents passing in the two adjacent tissue segments. This increases the current density in the neighbourhood of the electrode E itself and therefore the likelihood of its producing a rapid drying of the surrounding tissue. When this occurs, the impedance of the tissue in the neighbourhood of the electrode increases, thereby impeding the current to continue to flow; the current accordingly ceases in the intervals comprised between the intermediate electrode E and the adjacent electrodes. Hence, the entire region surrounding the electrode E itself, schematically denoted by RE in FIG. 1, becomes totally "isolated" from the electrocoagulation process under way, though actually the treatment has not been completed in correspondence of the entire extension of said region, but merely in close proximity of the electrode E and not yet in the zones farthest therefrom.

Moreover, the excessive drying in the neighbourhood of the internal electrodes produces a strong adhesion of the tissue surrounding them, making difficult their retraction from the coagulated tissue.

Due to the foregoing, it is often necessary to employ electrodes very close one to the other.

The present invention is based just on the detection of the hereto-described drawbacks.

Hence, the technical problem set and solved by the present invention is to provide an apparatus for electrosurgery and a related method enabling to overcome the drawbacks mentioned above with reference to the known art.

Such a problem is solved by an apparatus according to claim 1.

According to the same inventive concept, the present invention further relates to a method according to claim 26.

Preferred features of the present invention are present in the dependent claims thereof.

The present invention provides several relevant advantages.

The main advantage lies in that, thanks to the incremental powering of the electrodes, the invention enables to keep a current flow through tissues even when the intermediate electrode is deactivated, as it will be better understood from the following detailed description.

Moreover, current in the inter-electrodes intervals being equal, the current density and therefore the overheating in the neighbourhood of each electrode is markedly decreased.

All this enables to carry out a more effective electrosurgical treatment and to attain a more uniform result. Moreover, it is possible to reduce the number of electrodes employed, or anyhow, results being equal, to arrange them at a greater mutual distance with respect to the known art.

BRIEF DESCRIPTION OF THE SEVERAL
VIEWS OF THE DRAWING(S)

Other advantages, features and the modes of employ of the present invention will be made apparent in the following detailed description of some embodiments thereof, given as a non-limiting example. Reference will be made to the figures of the attached drawings, wherein.

DETAILED DESCRIPTION OF THE INVENTION

Figure 2:
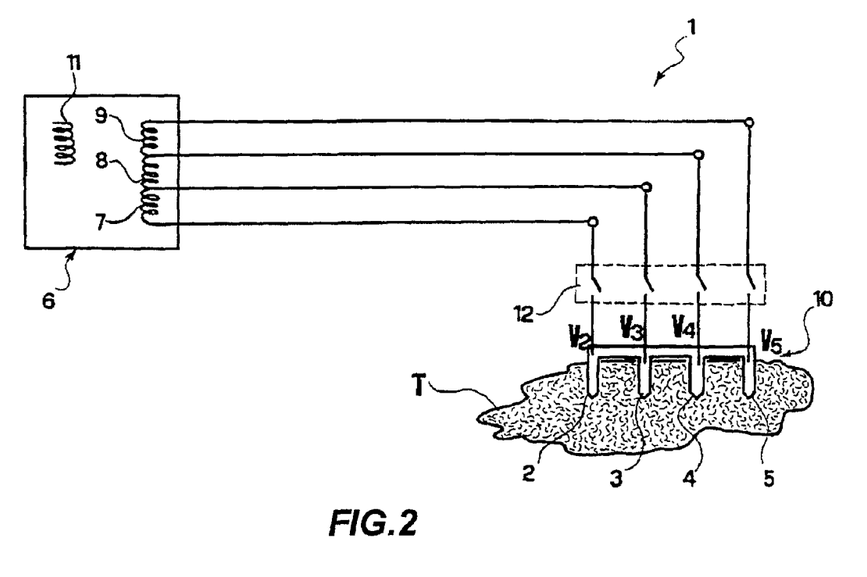
FIG. 2 shows a schematic depiction of an embodiment of an apparatus for electrosurgery according to the present invention.

With reference to FIG. 2, an apparatus for electrosurgery according to an embodiment of the invention is globally denoted by 1. The apparatus 1 comprises a plurality of adjacent electrodes, and in particular four, denoted by 2, 3, 4 and 5, respectively. In the present embodiment the electrodes 2-5 are the arms of a comb device generally denoted by 10. The electrodes 2-5 are therefore arranged substantially aligned, and in FIG. 2 they were depicted in an operating configuration inserted in a tissue T.

Variant embodiments may provide the employ of independent electrodes, i.e. not constrained to the same support, arranged in a sequence but not necessarily along a straight line. Of course, also the number of electrodes may vary according to specific treatment needs.

The electrodes 2-5 are powered by means for generating an electrosurgical current, generally denoted by 6, apt to induce the flowing of an electrosurgical current through the tissue portions interposed thereamong. In particular, the means 6 power the electrodes 2-5 so that each electrode has a potential greater than that of the electrode preceding it in the sequence. Therefore, with reference to the embodiment of FIG. 2, the potential $V_3$ of the second electrode 3 is greater than the potential $V_2$ of the first electrode 2, and likewise $V_3 < V_4 < V_5$.

The optimum incremental values to be used will depend on the impedance provided between the successive electrodes, so that, called:

$Z_{2-3}$ the impedance between electrodes 2 and 3,
$Z_{3-4}$ the impedance between electrodes 3 and 4,
$Z_{4-5}$ the impedance between electrodes 4 and 5
and
$V_{2-3}$ the difference in potential between $V_3$ and $V_2$,
$V_{3-4}$ the difference in potential between $V_4$ and $V_3$,
$V_{4-5}$ the difference in potential between $V_5$ and $V_4$,
it is obtained:

$$V_{2-3}/Z_{2-3} = V_{3-4}/Z_{3-4} = V_{4-5}/Z_{4-5} = I.$$

Thus, in the electrodes 2 and 5 and in all of said impedances the current I will be attained, whereas in the electrodes 3 and 4 the resulting current will be zero.

As it is well-known to the person skilled in the art, the generating means 6 is apt to power the electrodes with alternating voltage.

In the present embodiment, said incremental powering of the electrodes 2-5 is obtained by connecting each pair of adjacent electrodes 2-3, 3-4 and 4-5 to the ends of a respective secondary transformer circuit 7-9 of the means 6. Said secondary circuits 7-9 are in turn power-fed by a common primary circuit 11. As the circuits at issue are well-known to a person skilled in the art, they have been depicted purely by way of example in FIG. 2.

An alternative embodiment of the invention provides instead a powering of the electrodes by distinct generators, connected in series, for each pair of adjacent electrodes, so as to enable a simpler individual adjusting of the difference in potential between the electrodes, so as to keep unvaried the intensity of the current flowing in the various tissue segments in the presence of different impedances between the individual segments.

The apparatus 1 is also equipped with activating/deactivating means 12, apt to selectively connect/disconnect each electrode 2-5 to/from the generating means 6 when the tissue region surrounding the electrode itself has been completely treated, so as to avoid an excessive drying and the ensuing excessive adhesion of the treated tissue to the electrode, or also to meet specific treatment needs. Said activating/deactivating means 12 may be implemented in a known manner, via a set of switches controlled by a central processing unit of the apparatus 1 and/or directly by an operator, therefore a further description thereof will be omitted.

Figure 3A:
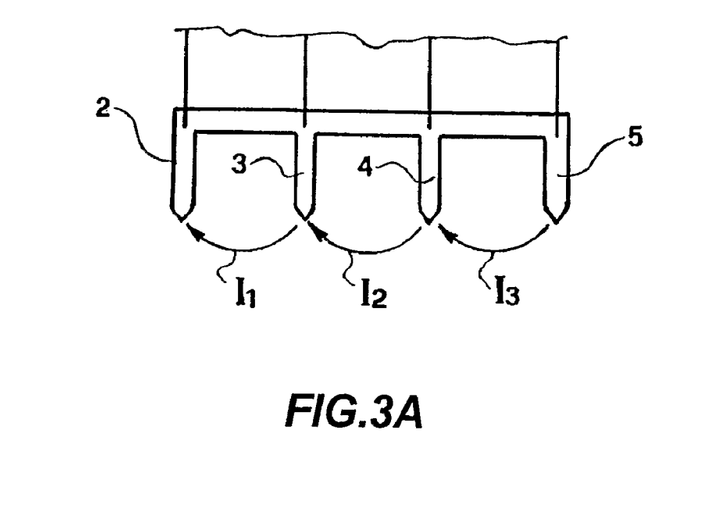
FIG. 3A shows a schematic depiction of a first operating configuration of the electrodes of the apparatus of FIG. 2.

FIG. 3A shows the electrodes 2-5 in a configuration in which they are simultaneously active, as occurs, e.g., at the start of the treatment. The main current lines are those between each pair of adjacent electrodes 2-3, 3-4 and 4-5, and have been denoted by $I_1$, $I_2$ and $I_3$, respectively.

Figure 3B:
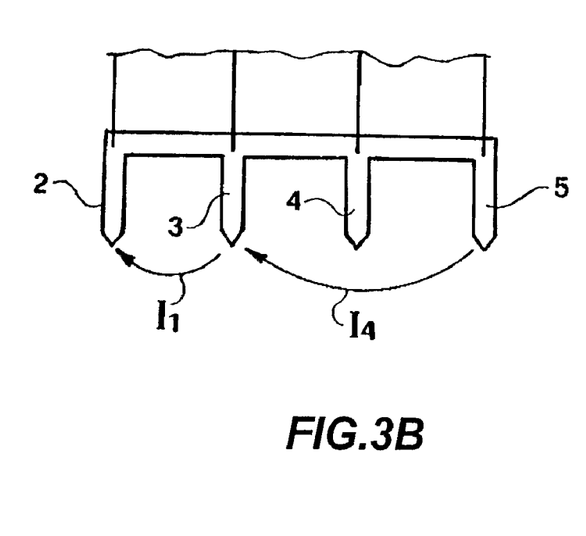
FIG. 3B shows a schematic depiction of a second exemplary operating configuration of the electrodes of the apparatus of FIG. 2.

FIG. 3B is instead a schematic depiction of the configuration of current onsetting when an intermediate electrode, e.g. the electrode 3, is deactivated. As just shown by way of example in this latter figure, also in this state it is possible to keep an electrosurgical current $I_4$ in the region surrounding the electrode 3 itself. In fact, by virtue of the incremental powering of the electrodes themselves, between the electrode 2 immediately preceding and the electrode 4 immediately successive to the deactivated electrode 3, an electrosurgical current flow onsets anyhow, to the advantage of the completeness of treatment of the concerned region. Moreover, it is possible to keep said current even when two adjacent electrodes of the sequence, e.g. the electrodes 3 and 4, are deactivated; in this case, in the example considered here, an electrosurgical current onsets between the end electrodes 2 and 5.

Lastly, the apparatus 1 provides also means apt to power the electrodes 2-5 with a pulse of current of a intensity greater than that previously used for the treatment, and this typically at the end of the treatment to definitively stabilize the attained result and obliterate for instance blood vessels of greater diameter the coagulation of which has not previously intervened during the treatment.

Figure 4A:
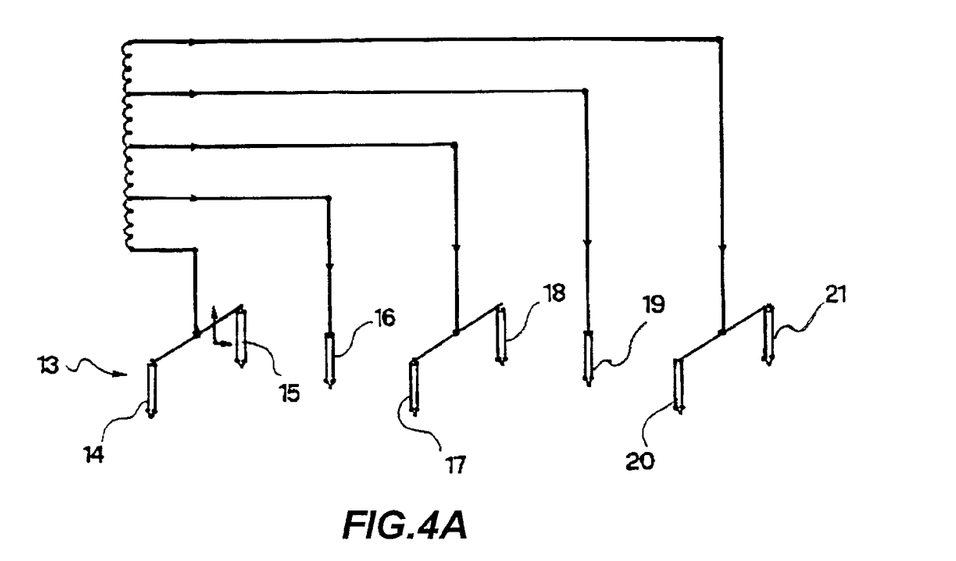
FIGS. 4A and 4B show a schematic perspective view and a top plan view of an electrode configuration of a second embodiment of the invention, respectively.
Figure 4B:
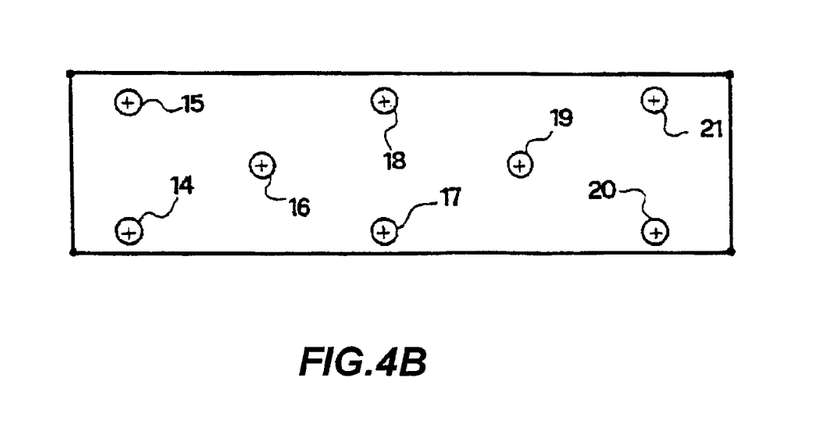

According to a second embodiment, shown in FIGS. 4A and 4B, it is provided a bidimensional comb electrode, generally denoted by 13. In particular, the comb electrode 13 of the present embodiment comprises eight electrodes, denoted by 14, 15, 16, 17, 18, 19, 20 and 21, respectively, arranged so that groups of three adjacent electrodes define the vertexes of a substantially isosceles or equilateral triangle. Hence, the electrodes 14-21 are not arranged in-line, but rather define a bidimensional configuration enabling indeed to carry out a bidimensional resection. Said electrodes 14-21 are then fed according to the incremental voltage of the invention. In particular, the electrodes of each pair 14-15, 17-18 and 20-21 are fed according to a respective common voltage, $V_{45}$, $V_{78}$ and $V_{01}$, respectively, and the intermediate electrodes 16 and 19 with respective voltages $V_{16}$ and $V_{19}$, so that:

$$V_{45} < V_{16} < V_{78} < V_{19} < V_{01}.$$

This electrode configuration enables to obtain a coagulated-tissue portion substantially rectangular- or parallelepiped-shaped with a rectangular plan, whereas with a comb having in-line (aligned) electrodes the plan of the resection obtained with two successive and parallel applications of the electrode itself tends to be elliptical. Hence, with the proposed bidimensional configuration it is attained a more uniform width of coagulated tissue with respect to that attainable with a linear comb, the latter tending to be inferior in width at the ends with respect to the center.

For the other elements, the apparatus of the present embodiment is analogous to that described above with reference to FIGS. 1 to 3B.

According to a variant embodiment compatible with both the embodiments described above and shown in FIG. 6, the apparatus of the invention may comprise means 100 for measuring the intensity of the current delivered by each electrode during the treatment. In said FIG. 6 the means for generating an electrosurgical current and the electrodes are analogous to those of the first embodiment and therefore have been denoted by the same reference numbers 6 and 2-5, respectively.

Figure 6:
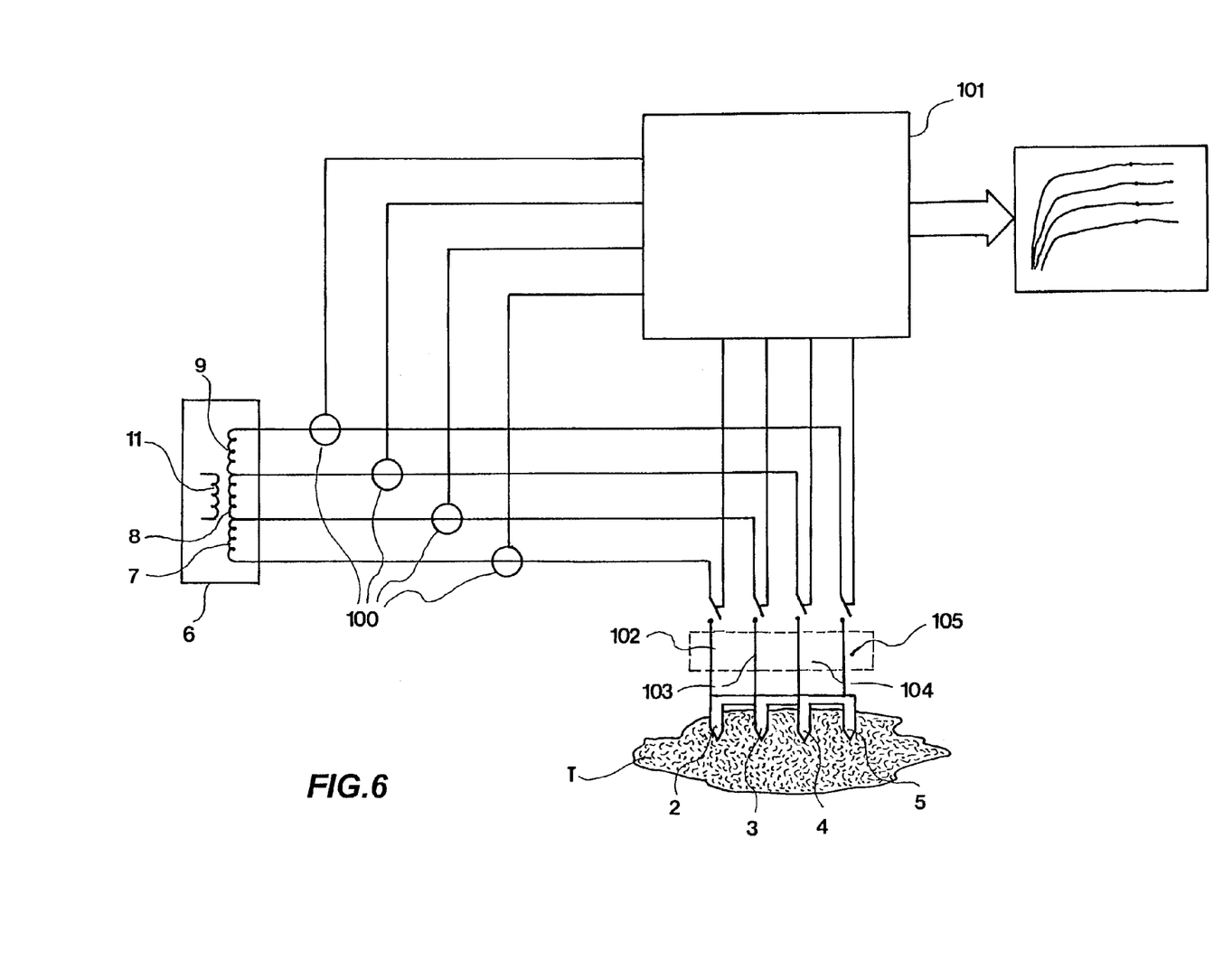
FIG. 6 shows a schematic depiction of another embodiment of an apparatus for electrosurgery according to the present invention.

The means 100 may be implemented by electric current transformers arranged at the connection of each electrode 2-5 to the current generating means 6.

The means 100 may carry out the measuring continually or at predefined time intervals, optionally settable by the operator.

Preferably, the measuring means 100 is connected to a control unit of the apparatus or anyhow to control means 101 apt to automatically disconnect an electrode 2-5 from the current generating means 6 when the corresponding detected current intensity drops below a predefined threshold. In particular, said threshold may be a preset fraction of the maximum value of current foreseen or reached. This is so since, as illustrated in the foregoing, the reduction of the current intensity concerning each electrode is related to the impedance increase ensuing from the drying of the tissue in the neighbourhood of the electrode itself. Therefore, a timely disconnection of the electrode from the generating means contributes to prevent the excessive adhesion of the electrode to the tissue, accordingly promoting its retraction at the end of the treatment.

Said disconnection may be carried out through a set of switches 102-105 placed each at a respective electric connection of an electrode 2-5 to the control unit 101.

Said continual measuring of the current delivered by each electrode enables also the detaching of the electrode itself when said delivered current does not reach at least a predetermined and optionally preset minimum value. Thus, it is enabled the disconnection, optionally automatic by means of said control unit or means 101, of any electrode not actually inserted in the tissue voluntarily or by mistake, e.g., due to a linear dimension of the instrument greater than the linear dimensions of the tissue to be treated. Even this disconnection may be carried out through the set of switches 102-105.

As it is shown always in FIG. 6, the control unit 101 may also provide the operator with an output, e.g. of a graphic type, related to the current measured at each electrode 2-5.

Figure 5A:
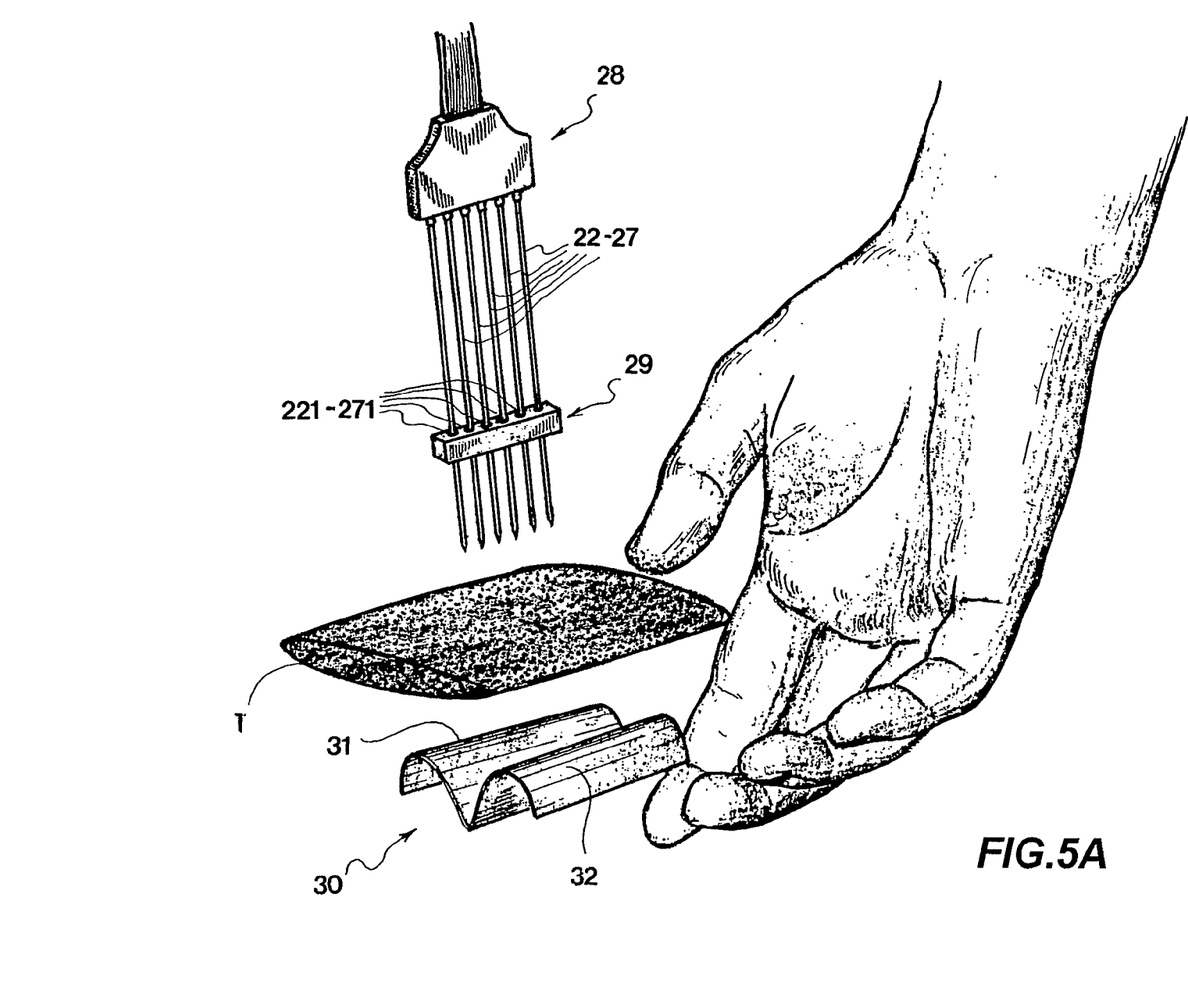
FIGS. 5A and 5B show a side perspective view and a front perspective view, respectively, of additional optional components of the apparatus of FIG. 1 or FIG. 4A during surgery.
Figure 5B:
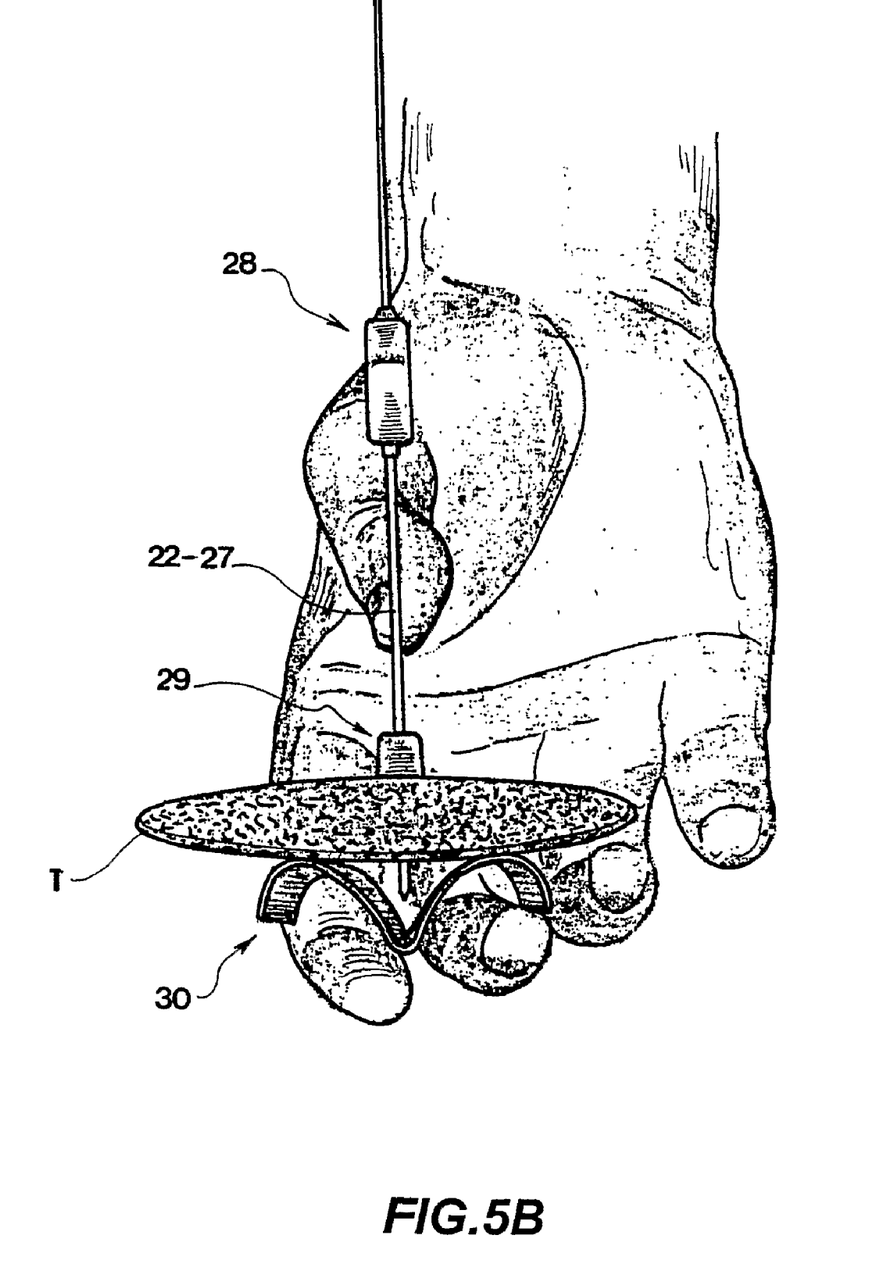

According to a further variant of the invention, it also compatible with what has been described hereto and shown in FIGS. 5A and 5B, the apparatus comprises a slidable guide 29 apt to facilitate the insertion of the electrodes, which in the embodiment proposed in said figures are six and denoted by numbers 22 to 27, respectively. Said electrodes 22-27 are, in this example as well, arms of a comb device, here denoted by 28. The guide 29 has a plurality of through seats, in particular six seats denoted by numbers 221 to 271, respectively, each apt to receive a respective electrode 22-27.

The guide 29 is apt to keep in a substantially parallel position the electrodes during the insertion in a tissue T, preventing them from flexing and accordingly from modifying the relative distance between pairs of adjacent electrodes. In the present embodiment, the guide 29 is apt to keep parallel the aligned electrodes 22-27.

Moreover, a further variant, shown always in FIGS. 5A and 5B, provides that the bottom of the parenchyma be supported by fingers protected by a protection device 30, it also apt to facilitate the insertion of the electrodes 22-27 in the tissue T. The device 30 is preferably piece-formed and it comprises a pair of thin side-by-side elements, denoted by 31 and 32, respectively, each having a curved contour apt to receive a finger and substantially reproducing the outline thereof. Preferably, said elements 31 and 32 are apt to receive forefinger and middle finger, as shown in FIG. 5B.

The elements 31 and 32 are made of an insulating material (e.g. ABS) biocompatible and preferably resistant to a minimum temperature of 100° C., so as to be kept in situ during the delivery.

The device 30, besides from protecting the operator's fingers, protects also the underlying tissues from a casual unintentional pricking due to the electrodes 22-27 emerging from the entered tissue, thereby implementing means apt to this purpose. Moreover, the device 30 also prevents the heating of said underlying tissues.

Therefore, it will be understood that the guide 29 and the device 30 implement, jointly as well as individually, means for facilitating and making safe the insertion of the electrodes into the tissue. Said guide 29 and device 30 may even be employed and considered individually and optionally independently from the apparatus of the invention described hereto.

As mentioned above, the device 30 implements also means apt to protect the tissues underlying that concerned by surgery from the pricking due to the insertion of the electrodes 22-27 in the tissue to be treated.

The invention further relates to a method for the carrying out of an electrosurgical treatment employing a plurality of adjacent electrodes, e.g. as the abovedescribed ones, arranged in sequence and powered so as to induce the flowing of an electrosurgical current through the tissue portions interposed thereamong. As already described hereto, the powering of said electrodes provides that each electrode has a potential greater than that of the electrode preceding it in the sequence, according to the modes illustrated above with reference to apparatus 1.

Of course, the method at issue can be implemented by an apparatus as the one described above.

The present invention has hereto been described with reference to preferred embodiments thereof. It is understood that there could be other embodiments afferent to the same inventive kernel, all falling within the protective scope of the claims hereinafter.

The invention claimed is:

1. An apparatus for electrosurgery, comprising:
   at least three adjacent electrodes arranged in sequence; and
   electrosurgical current generating means, connected to said electrodes to induce the flowing of an electrosurgical current through the tissue portions interposed thereamong,
   wherein said electrosurgical current generating means incrementally powers said electrodes so that each electrode has a potential greater than that of each electrode preceding it in the sequence.

2. The apparatus according to claim 1, wherein said electrodes are substantially aligned.

3. The apparatus according to claim 1, wherein said electrodes are part of a comb electrode.

4. The apparatus according to claim 1, wherein said electrosurgical current generating means comprises a plurality of secondary transformer circuits, each of said secondary circuits powering a respective pair of adjacent electrodes.

5. The apparatus according to claim 1, wherein said secondary transformer circuits are power-fed by a common primary circuit.

6. The apparatus according to claim 1, wherein said electrosurgical current generating means comprises a plurality of generators, each powering a respective pair of adjacent electrodes.

7. The apparatus according to claim 1, further configured for powering said electrodes with a current pulse having intensity greater than that previously used for the treatment.

8. The apparatus according to claim 1, comprising at least four of said electrodes including a first electrode, a last electrode, and intermediate electrodes, wherein said electrosurgical current generating means powers said electrodes so that in the intermediate electrodes of the sequence flows substantially no current.

9. The apparatus according to claim 1, wherein said electrodes are arranged according to a bidimensional configuration.

10. The apparatus according to claim 9, wherein said electrodes are arranged so that groups of three adjacent electrodes define the vertexes of a substantially isosceles or equilateral triangle.

11. The apparatus according to claim 9, wherein said electrodes are arranged so as to define a resection area having a substantially rectangular plan.

12. The apparatus according to claim 1, comprising measuring means for measuring the intensity of the current delivered by each electrode during the treatment.

13. The apparatus according to claim 12, wherein said measuring means carries out said measuring continually or at predefined time intervals.

14. The apparatus according to claim 12, comprising control means for automatically disconnecting an electrode from said current generating means when the corresponding current intensity detected by said measuring means is lower than a predefined threshold.

15. The apparatus according to claim 14, wherein said predefined threshold is a preset fraction of the maximum value of current foreseen or reached.

16. The apparatus according to claim 12, comprising control means for providing the disconnection of an electrode from said current generating means when the current measured by said measuring means is lower than a preset minimum value.

17. The apparatus according to claim 1, comprising means for facilitating the insertion of the electrodes in a tissue.

18. The apparatus according to claim 17, wherein said means for facilitating the insertion of the electrodes in a tissue comprises a slidable guide that keeps the electrodes in a substantially parallel position during the insertion in the tissue.

19. The apparatus according to claim 18, wherein said slidable guide prevents flexing of the electrodes during the insertion in the tissue.

20. The apparatus according to claim 18, wherein said guide has a plurality of seats each receiving a respective electrode.

21. The apparatus according to claim 17, wherein said means for facilitating the insertion of the electrodes in a tissue comprises a protection device for an operator's fingers.

22. The apparatus according to claim 21, wherein said device comprises a pair of elements each configured to receive a finger.

23. The apparatus according to claim 22, wherein each of said elements has a curved contour.

24. The apparatus according to claim 22, wherein said elements are configured to receive a forefinger and a middle finger, respectively.

25. The apparatus according to claim 1, comprising means for protecting the tissues underlying that concerned by surgery from a pricking due to the insertion of the electrodes into the tissue to be treated.

26. A method for the carrying out an electrosurgical treatment, employing at least three adjacent electrodes arranged in sequence and powered so as to induce a flowing of an electrosurgical current through tissue portions interposed thereamong,
wherein powering of said electrodes is effected incrementally such that each electrode has a potential greater than that of each electrode preceding it in the sequence.

27. The method according to claim 26, wherein said electrodes are substantially aligned.

28. The method according to claim 26, wherein said electrodes are part of a comb electrode.

29. The method according to claim 26, wherein pairs of adjacent electrodes are powered by a respective secondary transformer circuit.

30. The method according to claim 29, wherein said secondary transformer circuits are power-fed by a common primary circuit.

31. The method according to claim 26, wherein pairs of adjacent electrodes are powered by a respective electrosurgical current generator.

32. The method according to claim 26, comprising providing, at the end of the treatment, a powering of said electrodes with a pulse of current of an intensity greater than that previously used for the treatment.

33. The method according to claim 26, which is a treatment preliminary to resection.

34. The method according to claim 26, comprising at least four of said electrodes including a first electrode, a last electrode, and intermediate electrodes, wherein the overall arrangement is such that in the intermediate electrodes of the sequence flows substantially no current.

35. The method according to claim 26, wherein said electrodes are arranged according to a bidimensional configuration.

36. The method according to claim 35, wherein said electrodes are arranged so that groups of three adjacent electrodes define the vertexes of a substantially isosceles or equilateral triangle.

37. The method according to claim 35, wherein said electrodes are arranged so as to define a resection area having a substantially rectangular plan.

38. The method according to claim 26, comprising measuring an intensity of the current delivered by each electrode during the treatment.

39. The method according to claim 38, wherein said measuring is carried out continually or at defined time intervals.

40. The method according to claim 38, comprising providing the automatic interruption of the current feed of an electrode when the corresponding measured current intensity is lower than a predefined threshold.

41. The method according to claim 40, wherein said predefined threshold is a preset fraction of the maximum value of current foreseen or reached.

42. The method according to claim 38, comprising providing the automatic interruption of the current feed of an electrode when the measured current is lower than a preset minimum value.

43. The method according to claim 26, employing an apparatus for electrosurgery.

* * * * *